United States Patent [19]

Ray

[11] 4,094,328
[45] June 13, 1978

[54] DENTAL FLOSS MANIPULATING INSTRUMENT

[76] Inventor: Gerald E. Ray, Rte. 1, Wake Forest, N.C. 27587

[21] Appl. No.: 703,638

[22] Filed: Jul. 8, 1976

[51] Int. Cl.² .......................................... A61C 15/00
[52] U.S. Cl. .................................................. 132/91
[58] Field of Search .................................. 132/92, 91

[56] References Cited

U.S. PATENT DOCUMENTS

| 1,570,357 | 1/1926 | Lawrenz | 132/92 R |
| 2,381,530 | 8/1945 | Dembenski | 132/92 A |
| 2,544,276 | 3/1951 | Ness | 132/92 R |
| 3,340,881 | 9/1967 | Cowan | 132/92 R |
| 3,906,963 | 9/1975 | Jenkins | 132/91 |
| 3,939,853 | 2/1976 | Spanondis | 132/91 |

Primary Examiner—Louis G. Mancene
Attorney, Agent, or Firm—Mills & Coats

[57] ABSTRACT

In abstract, a preferred embodiment of this invention is an instrument for holding dental floss during the manipulation of the floss between the teeth of the user. This instrument is preferably in the form of a three pronged fork having a handle with a dental floss storage spool contained therein. A slide release for the spool feed and a cutter bar, along with floss guides are included. An alternate to the three pronged fork would be a stationary central fork with a releasably lockable, movable side fork which can be disposed alternately on either side of the center of the fork.

1 Claim, 10 Drawing Figures

DENTAL FLOSS MANIPULATING INSTRUMENT

This invention relates to dental instruments and more particularly to dental floss manipulating devices.

In the past, various types of devices, sometimes called dental floss holders have been developed in an attempt to ease the effort required in removing foreign particles from between the teeth by passing a strong strand or dental floss therebetween.

Although this procedure has been known, used and recommended for many years, only recently have dentists began recommending the use of dental floss between all of the teeth on a daily basis. This is commonly called "flossing the teeth" and is highly recommended by the American Dental Association.

Most people have trouble with the flossing procedure, particularly if they have large chubby hands, since the floss must be held taut on opposite sides of the teeth and then pushed down therebetween to the gum. Becuase of the natural difficulties this procedure requires, many people only partially floss their teeth or do not floss them at all.

Although a number of instruments have been developed and tested to aid in the manipulation of taut strand of dental floss between the teeth, particularly the back teeth, most of these devices have been in the form of a pair of symmetrical prongs which work well for some of the teeth but are almost impossible to manipulate between others.

After much research and study into the above mentioned problems, the present invention has been developed to provide a dental floss manipulating instrument which can readily be operatively positioned and used between all of the teeth of the user, front and back, uppers and lowers. In addition to the manipulation feature, the present invention has the additional advantages of providing a means for storing a supply of unused floss which, through a series of guides, can be fed to the tension area to replace the floss which has been used and become frayed or soiled. There is also provided a means in the form of a cutting bar for removing the used or soiled floss being replaced in the tension area.

In view of the above, it is an object of the present invention to provide a dental floss manipulating instrument having a three pronged floss tension fork on one end thereof.

Another object of the present invention is to provide a dental floss manipulating instrument including an unused floss storage means.

Another object of the present invention is to provide a dental floss manipulating instrument including a dental floss holder in the handle thereof for lockingly storing a dental floss spool.

Another object of the present invention is to provide a quick release locking means for a dental floss spool.

A further object of the present invention is to provide a dental floss manipulating instrument including a plurality of guides for aiding in the replacement of used floss with new floss.

An even further object of the present invention is to provide a three pronged dental floss manipulating instrument having a floss storage compartment in the handle thereof and a cutter bar for removing used floss from the instrument.

Another object of the present invention is to provide a two pronged dental floss manipulating instrument with one of the prongs being movable from one side to the other to allow manipulating use thereof in the same manner as a three pronged floss fork.

Other objects and advantages of the present invention will become apparent and obvious from a study of the following description of the accompanying drawings which are merely illustrative of such invention.

Figure 1:
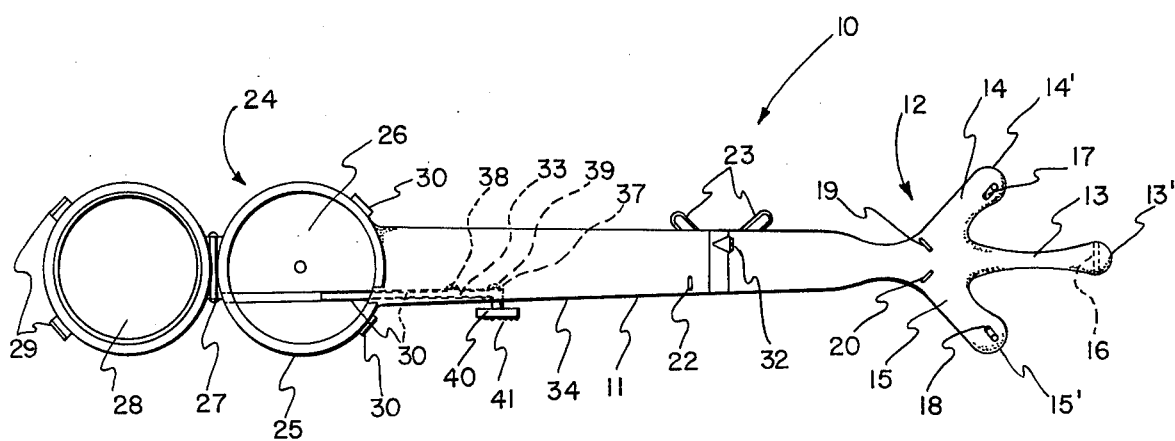
FIG. 1 is a top plan view, as oriented in the drawings, of the dental floss manipulating instrument of the present invention without the floss threaded thereonto.
Figure 2:
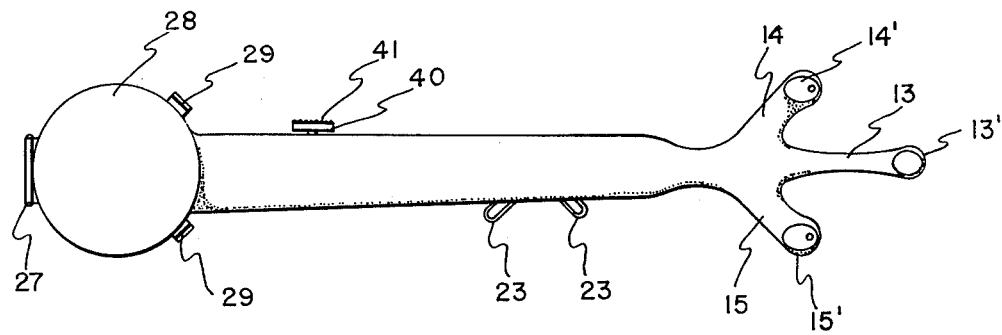
FIG. 2 is a bottom plan view of the instrument of the present invention as oriented in the drawings.
Figure 3:
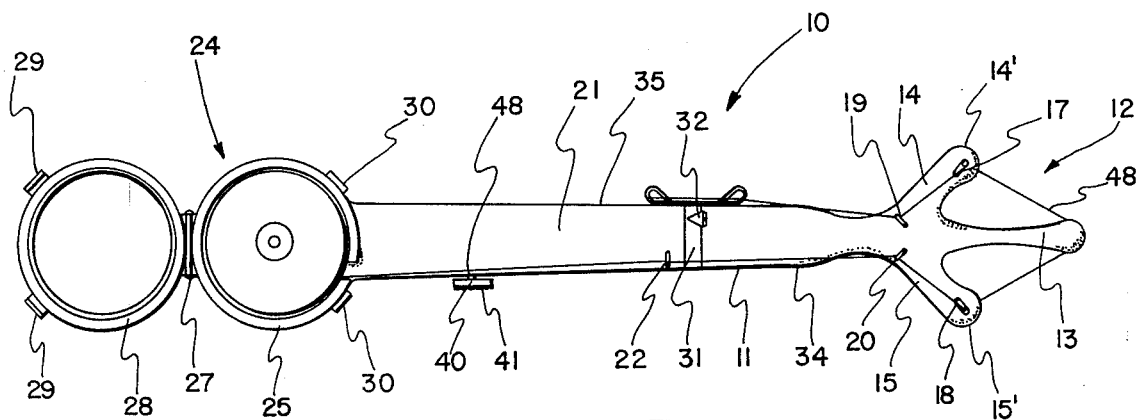
FIG. 3 is a top plan view of such instrument with the floss threaded in operative position.

With further reference to the drawings, the instrument of the present invention indicated generally at 10 includes an elongated handle or base portion 11. In the preferred embodiment, one end of this handle terminates in a fork-like configuration indicated generally at 12 and includes a central prong 13, and two side prongs 14 and 15. As can clearly be seen in the plain views of the drawings, the two side prongs protrude outwardly at approximately 90° angles to each other or 45° degrees on either side of the central prong. When viewed in the elevational views of the drawings, each of the prongs curves arcuately to form a finger-like configuration.

Disposed laterally through the outer tip 13' of central prong 13 is an opening 16. Passing longitudinally through the outer portions 14' and 15' of side prongs 14 and 15, respectively, are openings 17 and 18.

A pair of guides 19 and 20 are provided adjacent fork 12 on generally flat portion 21 of handle 11. Generally in the center of the flat portion 21 is provided a guide 22 for the purposes hereinafter set forth.

On side 35 of handle 11 in the central area thereof is provided a pair of outwardly disposed cleat-like ears or projections 23.

Either integrally formed with or fixedly secured to the end of handle 11 opposite fork 12 is a floss receptacle-dispenser indicated generally at 24. This receptacle-dispenser is preferably in the form of a generally cylindrical housing or wall portion 25 and a fixed end portion 26.

Secured adjacent the open end of cylindrical housing 25 is a hinge like pivot 27. Also, secured to hinge 27 in the normal manner is a lid or closure 28. A pair of outwardly projecting clasp means 29 are provided on the periphery of closure 28 in spaced relation to hinge 27 as can clearly be seen in FIG. 1. A pair of boss like projections 30 are provided on the exterior of housing 25 adjacent the open end of such housing and positioned such to cooperatively and frictionally engage clasps 29.

Figure 4:
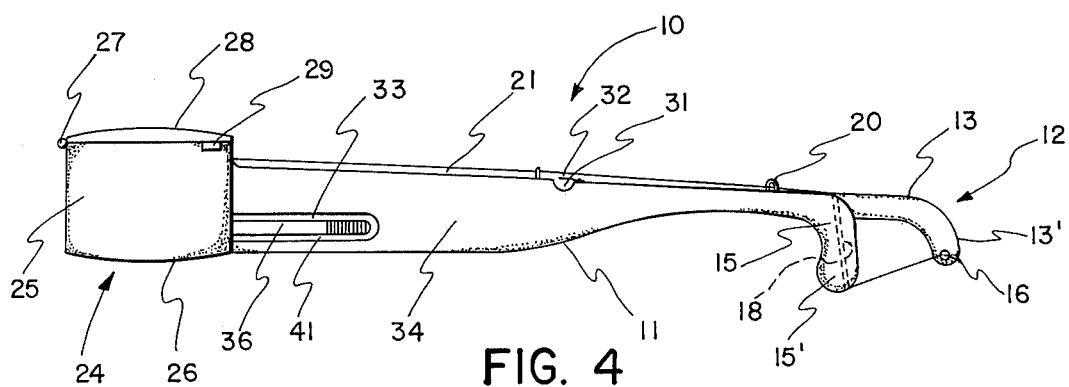
FIG. 4 is a side elevational view of the instrument of FIG. 3.
Figure 5:
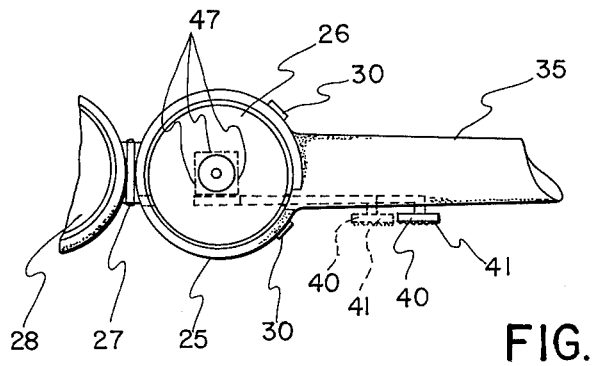
FIG. 5 is a detailed disclosure of the releasable floss storage spool locking means.
Figure 6:
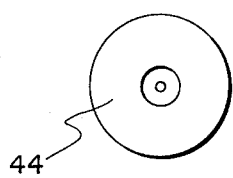
FIG. 6 is a top plan view of a typical floss spool used in conjunction with the present invention.
Figure 7:
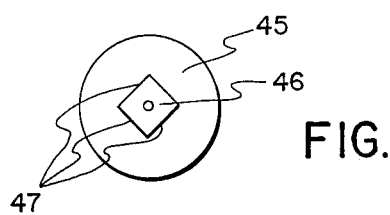
FIG. 7 is a bottom plan view of the same.
Figure 8:
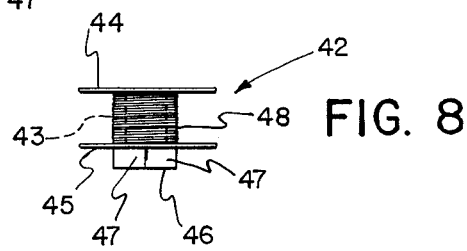
FIG. 8 is a side elevational view of such spool.

From the above, it is obvious that closure or lid 28 can be pivoted to the open position shown in FIG. 1 or to the closed position shown in FIG. 4 as desired with the clasp means holding the lid in retained closed condition.

A slot like opening 25' is provided in housing 25 adjacent the open end thereof to allow the floss carried within the housing to be fed therefrom as will hereinafter be described in more detail.

A recess or trough like slot 31 is disposed laterally across a flat portion 21 of handle 11 in its central area. Projecting outwardly over slot 31 is a cutter bar 32. The function of this cutter bar will become more apparent from the description of the use of the instrument of the present invention.

An elongated slot 33 is provided in side wall 34. This slot 33 extends from the interior of housing 25 to a point approximately one-third of the distance between such housing and fork 12. This slot, upon entering housing 25, is preferably at least partially grooved in the interior portion of end 26 as can clearly be seen in FIG. 1. A locking bar 36 is provided which is so sized as to snugly but freely be mountable in slot 33. This locking bar has on its most interior surface a boss-like member 37 which is adapted to releasingly engage dimples 38 and 39 at the locking bar's two extremities of longitudinal travel.

A locking bar manipulating handle 40 is secured to said bar at its end opposite the portion disposed within housing 25. This handle preferably has a serrated or high friction coefficient surface 41 provided thereon to aid in the operation of the same.

The dental floss storage spool, indicated generally at 42, includes a core 43 with generally flat circular end portions 44 and 45 fixedly secured thereto. On the side of end 45 opposite core 43 is a flat sided projection 46 preferably of hexagonal shape although certainly almost any flat configuration would suffice. Spool 42 is adapted to be inserted into housing 25 with projection 46 lying juxtaposed to end 26. Thus, it can be seen that when locking bar 36 is slidingly moved to its limit of travel in the direction of fork 12, spool 42 can freely rotate within housing 25; but when locking bar 36 is moved to its limit of travel in the opposite direction, said locking bar will engage one of the surfaces 47 of spool projection 46 to effectively lock said spool from rotation.

To use the dental floss manipulating instrument of the present invention, first a spool 42 of the type described is inserted into housing 25 and the floss 48 coiled on said spool is unwound for a short length. The floss is pulled out of said housing through opening 25' and lid 28 is closed. Pressure is then applied to the exterior thereof to frictionally engage clasp means 29 with boss means 30.

The floss is then threaded through guide 22, guide 20 and opening 18 in prong 15. The floss passes out of end 15' of prong 15 and through opening 16 of prong 13. Then it enters opening 17 at the tip 14' of prong 14 and passes through guide 19.

Some amount of excess floss is then pulled through the guides and openings as hereinabove described and handle 40 is used to slide locking bar 36 into engagement with one of the surfaces 47 of spool projection 46, thus locking said spool against further rotation.

The excess floss is then pulled taut thus pulling against spool 42 through the guides and openings so that the floss extending between the tips of prongs 15 and 13, and 13 and 14 is taut. The excess floss is then wound around the cleat projections 23 on side 35 of instrument 10 to not only secure the end of the floss but also to maintain tautness of such floss.

Once the floss has been cleated, if there is excess left over it, can be placed in slot to trough 31 and then pulled back against cutter bar 32 to sever the same.

Figure 10:
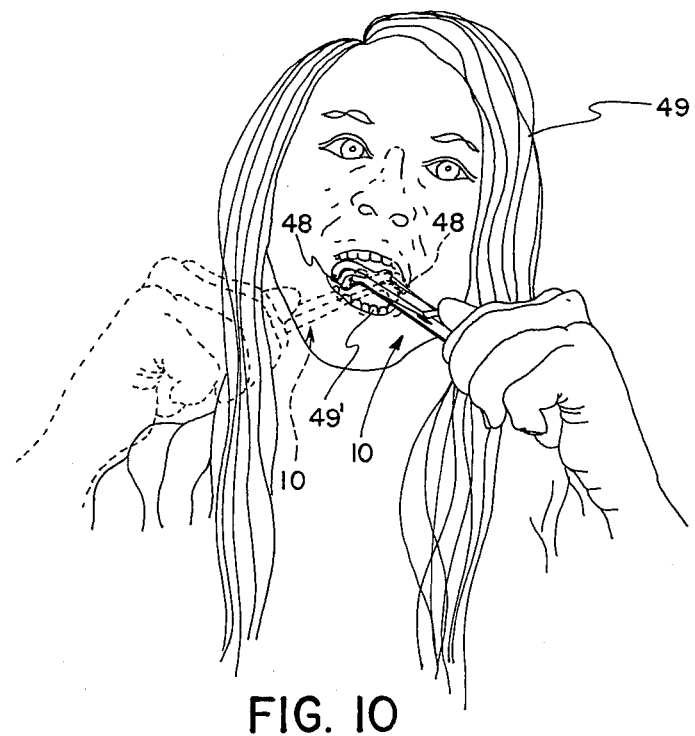
FIG. 10 is a perspective view of the instrument of the present invention in actual use.

The dental floss manipulation instrument of the present invention is then ready to floss the teeth 49' of the user 49. Depending on which teeth, either right or left, are being flossed, and depending on whether they are uppers or lowers, the instrument of the present invention can quickly and readily be manipulated so that the floss 48 tensioningly held between the prongs of fork 12 can be moved between each adjoining tooth to clean therebetween and remove foreign particles therefrom. Two different positions are shown in FIG. 10 as exemplary of the flossing operation when using the instrument of the present invention.

When the tensioned floss between the prongs becomes fray or soiled (as by foreign substances or bleeding of the gum of the user), the cleated end of the floss is unwound from projections 23 and locking bar 36, through manipulation of handle 40, is slid to release spool 42. As the locking bar is moved, box 37 will be disengaged from dimple 38 (locked position) and will engage dimple 39. Spool 42 is then free to rotate and when the floss adjacent the cleat 23 is pulled, the frayed, worn or soiled floss between the prongs will pass through guides 19 and can be removed by continued pulling until clean floss is adjacent cutting bar 32. This cutter bar can then be used to sever the frayed or soiled portion of floss. Some additional floss is pulled out to have an excess, then locking bar 36 is again engaged with spool 42 and the loose end of the floss is tauntly pulled around cleating ears 23. Thus the dental floss manipulating instrument is very simply and quickly ready for further use by user 49.

Figure 9:
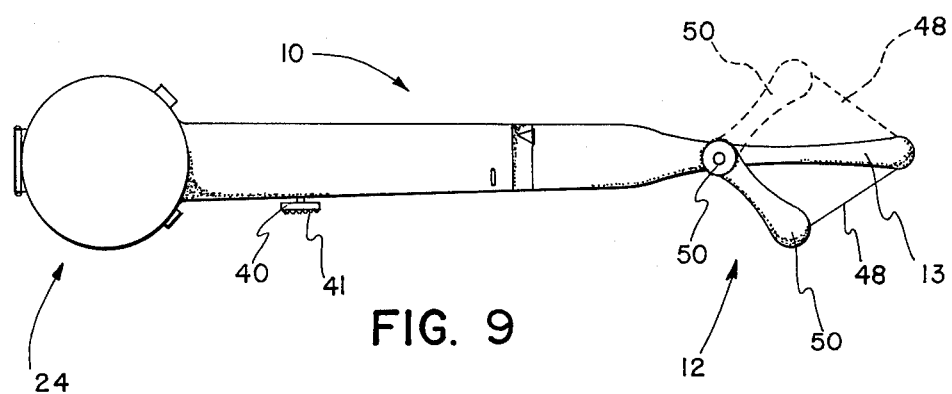
FIG. 9 is a top plan view of the movable fork modification of the present invention.

Operation of the modification shown in FIG. 9 is the same as hereinabove described except locking screw 51 is loosened when all the teeth on one side have been cleaned and the pivotable prong 50 is swung 90° to the approximate 45° position on the opposite side of central prong 13 from its original position. The floss is then again tensioned through the use of the cleat and spool locking means and further flossing can proceed.

In view of the above, it is obvious that the present invention provides a simple and yet highly efficient means for performing the flossing operation on teeth with a minimum of effort on the part of the user. It is highly efficient in both the changing of the floss and in allowing the user of the same to reach usually difficult access areas of the mouth.

The terms describing the dental floss manipulating instrument and its parts have been used merely for convenience to describe the same as oriented in the drawings. It is to be understood, however, that these terms are in no way limiting since the invention by necessity must obviously be disposed in many different positions when used.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended Claims are intended to be embraced herein.

What is claimed is:

1. A dental floss manipulating instrument comprising: an elongated handle means; a fork means at one end of said handle and including a central prong having a base portion adjacent said handle disposed in general longitudinal alignment with such handle; an elongated side prong pivotably connected at one end to the base portion of said central prong and being releasably pivotable from one side of said central prong to the other with an extreme limit of travel of approximately 90°, 45° on either side of said central prong; and means for tensioningly attaching a strand of dental floss between said central prong and said side prong whereby said instrument can be readily manipulated to dispose the floss between the teeth of the user of the same regardless of which side of the mouth is being flossed.

* * * * *